United States Patent
Faxe et al.

(10) Patent No.: US 6,572,165 B2
(45) Date of Patent: Jun. 3, 2003

(54) CONTACT LENS APPLIER, REMOVER AND CONTAINER

(76) Inventors: Thomas Faxe, Linde Allé 33, Dronning Mølle (DK), 3120; Per Faxe, Svinggårdsvej 1, Hornbæk (DK), 3100

( * ) Notice: Subject to any disclaimer, the term of this patent is extended or adjusted under 35 U.S.C. 154(b) by 0 days.

(21) Appl. No.: 10/162,781

(22) Filed: Jun. 4, 2002

(65) Prior Publication Data

US 2002/0158477 A1 Oct. 31, 2002

Related U.S. Application Data

(63) Continuation of application No. PCT/DK00/00673, filed on Dec. 6, 2000.

(30) Foreign Application Priority Data

Dec. 6, 1999 (DK) .......................................... 1999 01750

(51) Int. Cl.[7] .................................................. A61F 9/00
(52) U.S. Cl. .......................... 294/1.2; 294/25; 294/99.2; 206/5.1
(58) Field of Search .......................... 294/1.2, 25, 99.2; 206/5.1; 606/107, 210

(56) References Cited

U.S. PATENT DOCUMENTS

| | | | | |
|---|---|---|---|---|
| 2,462,208 A | * | 2/1949 | Meyer .............................. | 2/21 |
| 3,879,076 A | | 4/1975 | Barnett .................... | 294/1 CA |
| 4,126,345 A | * | 11/1978 | List .............................. | 294/1.2 |
| 4,190,277 A | * | 2/1980 | England ..................... | 294/1.2 |
| 4,545,478 A | * | 10/1985 | Waldman ..................... | 206/5.1 |
| 5,069,494 A | | 12/1991 | Reinson et al. .............. | 294/1.2 |
| 5,496,084 A | * | 3/1996 | Miralles Medan .......... | 294/1.2 |
| 5,879,038 A | | 3/1999 | Morgan ...................... | 294/1.2 |

FOREIGN PATENT DOCUMENTS

| | | | | |
|---|---|---|---|---|
| DE | 3822654 | | 1/1990 | |
| EP | 588434 | | 3/1994 | |
| GB | 2 328 924 A | | 10/1999 | |
| WO | WO 84/03435 | * | 9/1984 | ................. 294/1.2 |
| WO | WO 99/21519 | | 6/1999 | |

* cited by examiner

*Primary Examiner*—Dean J. Kramer
(74) *Attorney, Agent, or Firm*—Winston & Strawn

(57) ABSTRACT

A manipulator serving for applying a contact lens in or removing it from a user's eye. The manipulator is of the kind that includes a manipulation part for holding the manipulator with the fingers, a supporting part on the manipulation part with the same or a slightly smaller diameter than the contact lens, and a concave face on the supporting part for in use detachably receiving the contact lens. The manipulator furthermore includes a slit made in the supporting part and extending from its concave face. When the manipulator is used to remove a contact lens from an eye, the user presses the slit together a little so that a fold is preliminarily made with a subjacent channel for taking air from the open in under the loosened parts of the contact lens. Using the manipulator according to the invention, a contact lens can easily and safely be removed from a user's eye without risk of thereby injuring the cornea.

15 Claims, 7 Drawing Sheets

CONTACT LENS APPLIER, REMOVER AND CONTAINER

CROSS-REFERENCE TO RELATED APPLICATIONS

This application is a continuation of the US national phase designation of International application PCT/DK00/00673 filed Dec. 6, 2000, the content of which is expressly incorporated herein by reference thereto.

TECHNICAL FIELD

The invention relates to a manipulator for applying a contact lens in or removing a contact lens from a user's eye. This manipulator is of the type that includes a manipulation part for manipulating the manipulator with the fingers, a supporting part fitted on the manipulation part for supporting the contact lens in operation, and a concave face for receiving and detachably retaining the convex face of the contact lens.

BACKGROUND ART

For among other things cosmetic reasons, many prefer to use contact lenses instead of glasses. The user normally makes use of his fingers to apply or remove contact lenses at the risk of thereby bringing impurities and/or bacteria from the fingers onto the lens and/or into the eye.

With a view to remedy this disadvantage during application of a contact lens, an applicator described in U.S. Pat. No. 5,695,049 has been developed. This applicator has a concave, elastomeric disc for preliminarily holding the contact lens. With a finger under the disc, this elastomeric disc is then inverted so that it assumes a convex form with the contact lens placed on the now formed convex face of the disc. Finally, the contact lens is applied in the eye while the user's finger is placed under the disc. Neither this finger nor any other of the user's fingers will thereby come into contact with the contact lens or the eye, thus avoiding introducing contaminants into the eye.

During storing and distribution, the contact lens is lying together with sterile saline solution of suitable concentration in a bowl that the elastomeric disc forms in its original, concave form. The bowl is tightly sealed by e.g. a cap during storage.

The applicant has a previous International Patent Application, publication no. WO 99/21519, which is incorporated herein by reference thereto. This application discloses a package in form of a cup which is closely connected to a fingerstall for applying a contact lens into an eye. The package has a chamber with a sterile saline solution within which the contact lens lies. When the contact lens is to be used, the package is opened so that the contact lens is made to lie on a concave face on the fingerstall to which it adheres due to the surface tension in the saline solution. Then, the user uses the fingerstall to guide the contact lens into his eye where it will remain as the adhesive force between the eye and the contact lens is greater than the adhesive force between the lens and the concave face of the fingerstall.

The applicators disclosed in U.S. Pat. No. 5,695,049 and PCT Patent Application publication no. WO 99/21519 are not useful for removing a contact lens from an eye. However, such a device is known from U.S. Pat. No. 4,512,602 which functions with a suction disc at the end of a handle for handling the device during the operation. When the contact lens is to be removed, the suction disc is made to stick to the contact lens. Then, the user pulls at the handle of the device in order to thereby loosen and remove the stuck contact lens from the eye.

As a contact lens is stuck to the eye with a quite considerable adhesive force, there is thus a risk that this device will not only pull the contact lens free of the eye but that the cornea will more or less follow. Thus, the present invention seeks to provide an improvement over these known devices.

From European Patent Application 0588434 is known a contact lens fitter-remover having a rigid structure with to tweezer legs. Removal of an inserted contact lens is done by resting the ends of the legs on the contact lens, closing the legs so that by means of the transversal pressure exerted by the fingers, the lens bends slightly and become detached from the eye.

This rigid tweezer construction is difficult to manoeuvre during application and removal of the contact lens and the rigid edges of the end of the legs of the tweezer are likely to damage the contact lens. Consequently, this fitter-remover is unsuitable for reuseable lenses.

The present invention now provides a device that overcomes the problems of the prior art.

SUMMARY OF THE INVENTION

The present invention provides a manipulator for applying a contact lens in or removing a contact lens from a user's eye. This manipulator device is both easy and safe to use.

A plurality of such manipulators are conveniently provided in a single package. In addition, the invention provides a container for storing contact lenses.

The novel and unique features of the invention relate to the fact that the manipulator furthermore includes at least one slit made in the supporting part and extending from the concave face of this supporting part. When the manipulator is used to remove a contact lens from an eye, a part of the contact lens is preliminarily received as a fold in the slit whereby, between the eye and the contact lens, a channel is formed that ends in the open air. During the pulling off of the contact lens, this lens is gradually loosened from the eye while air is filled up under the loosened areas so that a negative pressure cannot be built here which in a harmful way could cause the cornea to completely or partly be loosened or pulled off the eyeball.

BRIEF DESCRIPTION OF THE DRAWINGS

The invention will be explained in greater detail below, describing only exemplary embodiments with reference to the drawing, in which.

DETAILED DESCRIPTION OF THE PREFERRED EMBODIMENTS

Figure 1:
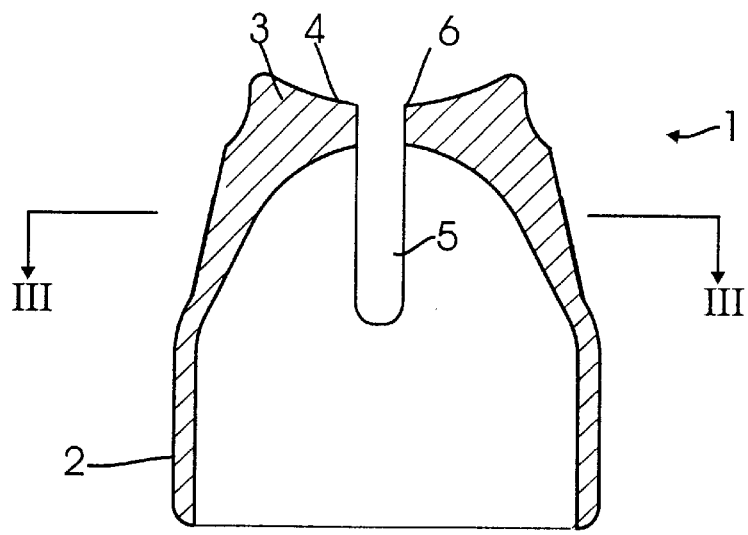
FIG. 1 is an axial sectional view of a manipulator according to the invention.

In a preferred embodiment, the manipulator is designed as a fingerstall with a skirt forming the manipulation part of the manipulator, and a base forming its supporting part whereby the slit is extending completely or partly through the base and a distance down along each side of the skirt. The fingerstall is simple and inexpensive to manufacture and easy to employ.

In its basic arrangement, the open slit end can move freely on the inside of the fingerstall. In other cases, it can however be advantageous to let the mouth of the slit on the inside of the fingerstall be closed by an elastically deformable wall which causes the base and sides of the fingerstall to be leakproof.

The elastically deformable wall can be designed as a U or a V extending all the way along the slit and with the legs connected to the inside of the fingerstall on both side of the slit. This embodiment is well suited for removing a contact lens by receiving the fold of the contact lens in the slit by pressing the manipulator a little together.

In order that the contact lens can be folded into the slit without being damaged, this slit can pass into the concave face of the manipulator along edges a slight curvature. These edges draw the part of the soft contact lens that is spanning the slit together in the direction of pressing.

The contact lens user may apply a convenient, empirically, self-chosen pressure/suction on both the lens and the eyeball when manipulating the contact lens during application and removal of the contact lens.

Contact lens users have different vaults of their eyeballs. To adapt the manipulator to different vaults, it is necessary to adjust the radius of the curvature of the concave face to each best individual fit. Such variable, adjustable radius of the curvature of the concave face of the supporting part of the manipulator is obtained by pressing at different preferred locations along the skirt thereby compressing the slit to different extents. Pressing near the concave face will provide a small radius and pressing at the skirt, e.g. near the bottom of the slit, provide a larger radius. The slit and the circumferential skirt provide a bellows-like construction making it flexible and possible to elastically adjust the radius.

It is preferred to manufacture the manipulator of a transparent elastically material so that the user can follow the orientation of the manipulator and the slit during application and removal of the contact lens.

In other cases, the elastically deformable wall can be designed as a membrane surrounding a channel connecting the underside of the base of the fingerstall to a slit only partly extending down into the base. The membrane acts as a vacuum pump which can provide a negative pressure for drawing a fold of the contact lens a little into the slit.

In an alternative embodiment, a liquid-absorbent material can be fitted into the slit for adhering to an area of the contact lens when this is to be removed from an eye.

The invention also relates to a package for containing a number of contact lenses. The novel and unique features according to the invention are that the package consists of a number of manipulators according to the invention which are joined in a row with a chamber for storing a contact lens defined by each of two adjacent manipulators. This package is very inexpensive as it only consists of the respective manipulators.

The invention furthermore relates to a container serving for storing a contact lens and comprising a manipulator according to the invention and a cap for closing the concave face on the base of the fingerstall. This container is well suited as package for a new contact lens and for subsequently, sterilely storing a reusable lens until it is to be used again.

Figure 2:
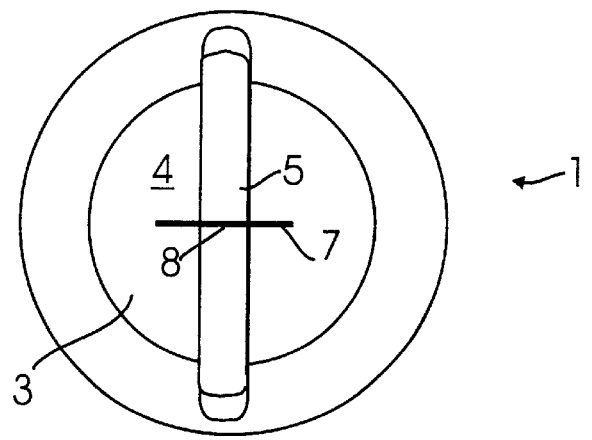
FIG. 2 is a plan view of the manipulator in FIG. 1.
Figure 3:
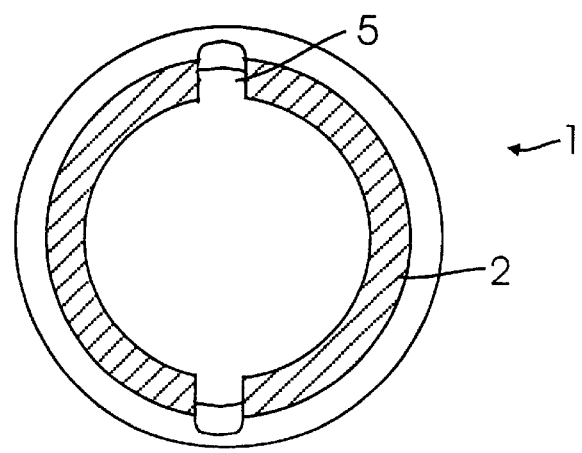
FIG. 3 is a sectional view taken along the line III—III of FIG. 1.

FIGS. 1 to 3 show a first embodiment of a manipulator 1 according to the invention. The manipulator has a skirt 2 and a base 3 with a concave face 4. Across the base and a distance down along each side of the skirt is made a slit 5. The edges 6 of the slit are provided with a small curvature to enable flexing of the face.

The manipulator can be made of any kind of suitable material. However, the material must be elastic for the manipulator to be able to obtain the desired effect. In the following, it is assumed that the manipulator is made of a plastic having the required elasticity and which furthermore is preferably transparent.

As shown in FIG. 2, a line of sight 7 is marked on the base 3, with the line passing through the center 8 of the base and across the slit 5 in cross direction. The line of sight 7 and the slit 5 together form a sight serving for facilitating the use of the manipulator.

Figure 4:
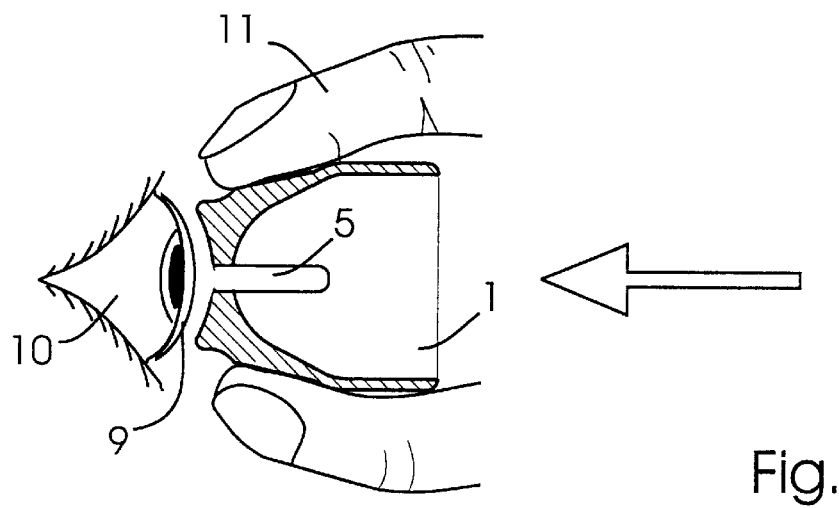
FIG. 4 is a fractional view of the manipulator in FIGS. 1 to 3 partly in section and in a first phase during removal of a contact lens from an eye.
Figure 5:
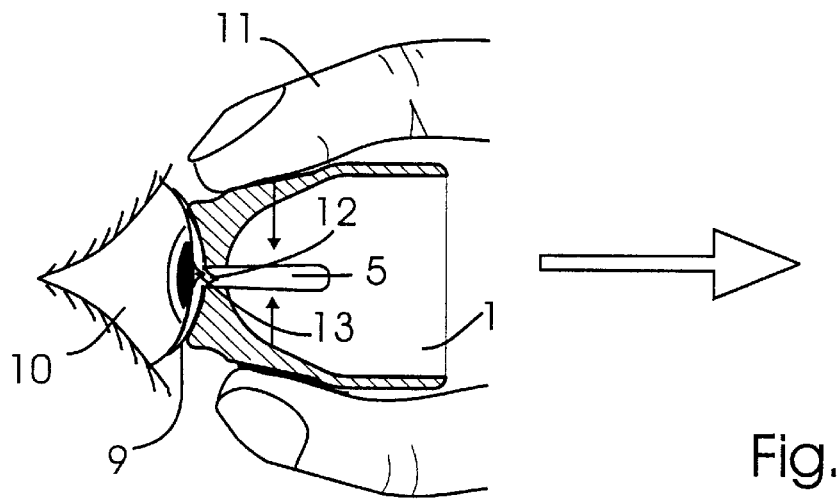
FIG. 5 is the manipulator in FIG. 4 in a second phase.
Figure 6:
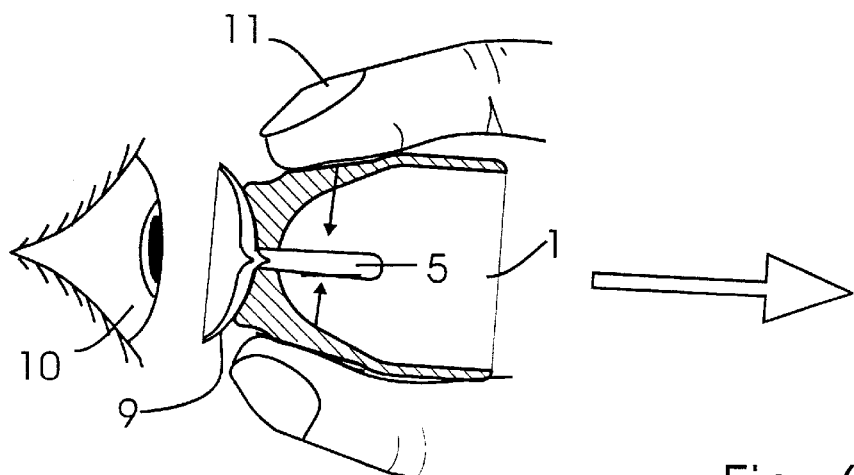
FIG. 6 is the manipulator in FIG. 4 in a third phase.

FIGS. 4 to 6 show how the user can use the manipulator to remove a contact lens 9 from an eye 10. In this Fig., the user's fingers grasp the manipulator 1 and guides it towards the eye in the direction indicated by the arrow. The user focuses his eye on the sight 5, 7 which is clearly outlined on the transparent base 3 and thereby securely guides the manipulator 1 into contact with the contact lens 9 as shown in FIG. 5.

In FIG. 5, the user now presses the slit a little in an area of the skirt in the middle of the slit 5, as indicated with the arrows. Thereby, the manipulator affects the soft contact lens with the edges 6 of the slit 5. As mentioned above, the edges have a small curvature, so that the contact lens is thereby drawn a little together in the direction of the arrows without being damaged. This results in a fold 12 being made in the slit 5, with the fold continuing out to the periphery of the contact lens and leaving behind it an air channel 13 between the eye and the contact lens. At the periphery of the contact lens, the air channel 13 ends in open air.

A contact lens adheres on the cornea of the eye with a relatively great adhesive force. If one attempts to pull the contact lens free of the eye, a negative pressure can be built between the cornea and the contact lens that together with the adhesive force can lead to the cornea being loosened and/or taken off when the contact lens is pulled free of the eye.

By using the manipulator according to the invention to remove the contact lens from the eye, this risk is completely eliminated as it now is not possible for a negative pressure to build up between the contact lens and the cornea.

For as described above, the channel 13 shown in FIG. 5 ends in the open and the pressure in the area of the contact lens under the fold 12 that is kept clear of adhesion is therefore always the same as the ambient pressure.

When the user now acts on the manipulator with a tractive effort in the direction indicated by the arrow in FIG. 5, that is away from the eye 10, the tractive effort is transmitted to the contact lens via both the fold 12 in the slit 5 and the adhesive force between the concave face 4 of the manipulator and the contact lens.

The user now pulls the contact lens free of the eye, as the already loosened area at the fold 12 successively extends to the rest of the contact lens during this action, with the growing space between the contact lens and the cornea successively being filled by air entering from the mouth of the space that is open to the atmosphere.

When the contact lens is removed by means of the manipulator according to the invention, the relatively great adhesion of the contact lens to the cornea therefore does not have to be overcome all at once at the risk of taking off the cornea. Instead, the contact lens is gradually loosened from the area at the fold with a tractive force that is quite insignificant in relation to the adhesive force existing between the cornea and the eyeball.

During this operation, a negative pressure furthermore cannot build up between the cornea and the contact lens as the air channel 13 under the fold 12 connects the areas under the loosened parts of the contact lent to the open from the start of the operation. By means of the manipulator according to the invention, a contact lens can therefore safely and effectively be removed from an eye without risk of thereby injuring the cornea of the eye.

In FIG. 6, the contact lens is now completely removed from the eye and is together with the manipulator taken away in the direction indicated by the arrow. The removed contact lens can be a disposable lens which is discarded after having been used only once, or a reusable lens which can be used many times. In the latter case, the contact lens is advantageously stored sterilely in a disinfectant fluid, for example sterile saline solution in suitable concentration, till the contact lens is to be applied in the eye again.

Figure 7:
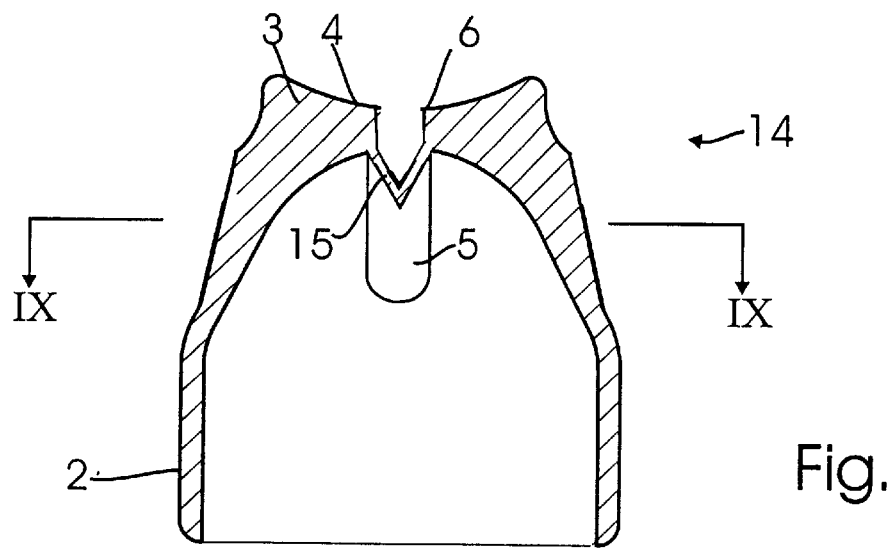
FIG. 7 is an axial sectional view of a second embodiment of a manipulator according to the invention.
Figure 8:
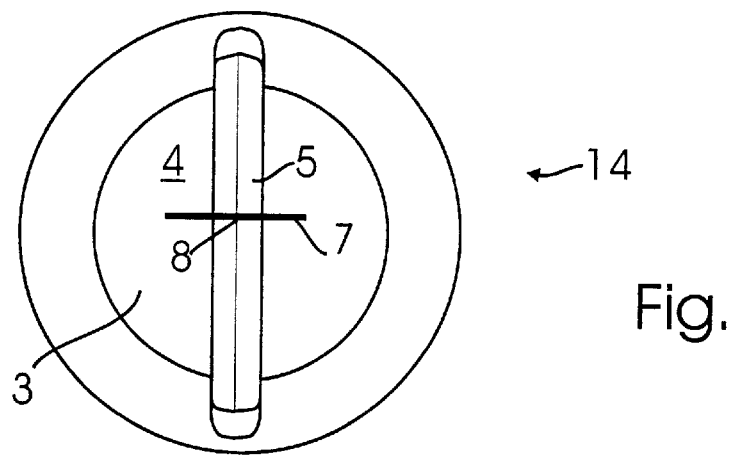
FIG. 8 is a plan view of the manipulator in FIG. 7.
Figure 9:
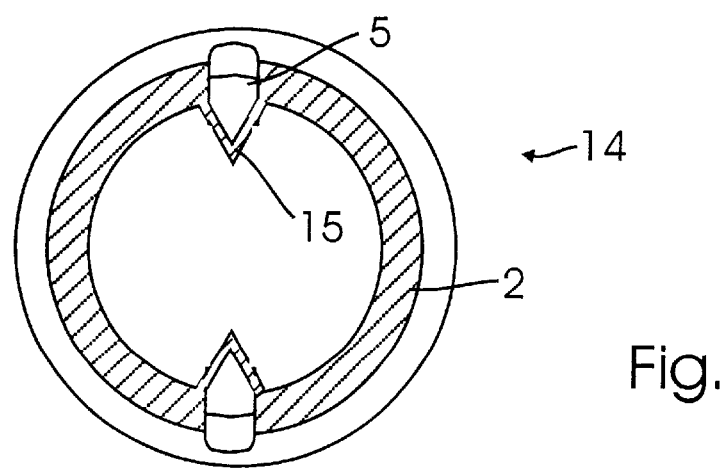
FIG. 9 is a sectional view taken along the line IX—IX of FIG. 7.

FIGS. 7 to 9 show a second embodiment 14 of a manipulator according to the invention in form of the manipulator shown in FIGS. 1 to 3 that now has been provided with a V-shaped wall 15 which on the inside of the manipulator is extending along the slit 5. The wall is in this case integral with the rest of the manipulator and is thus made of the same elastic material.

It is to be noted that the wall 15 alternatively can be joined with the manipulator and be made of a different material, for example rubber, and that the wall furthermore can have a shape different than a V, for example a U.

The elastic wall 15 allows the slit 5 to be pressed together and the manipulator to function in the same way as shown in FIGS. 4 to 6 and described above. This function therefore need not be mentioned any further here.

Figure 10:
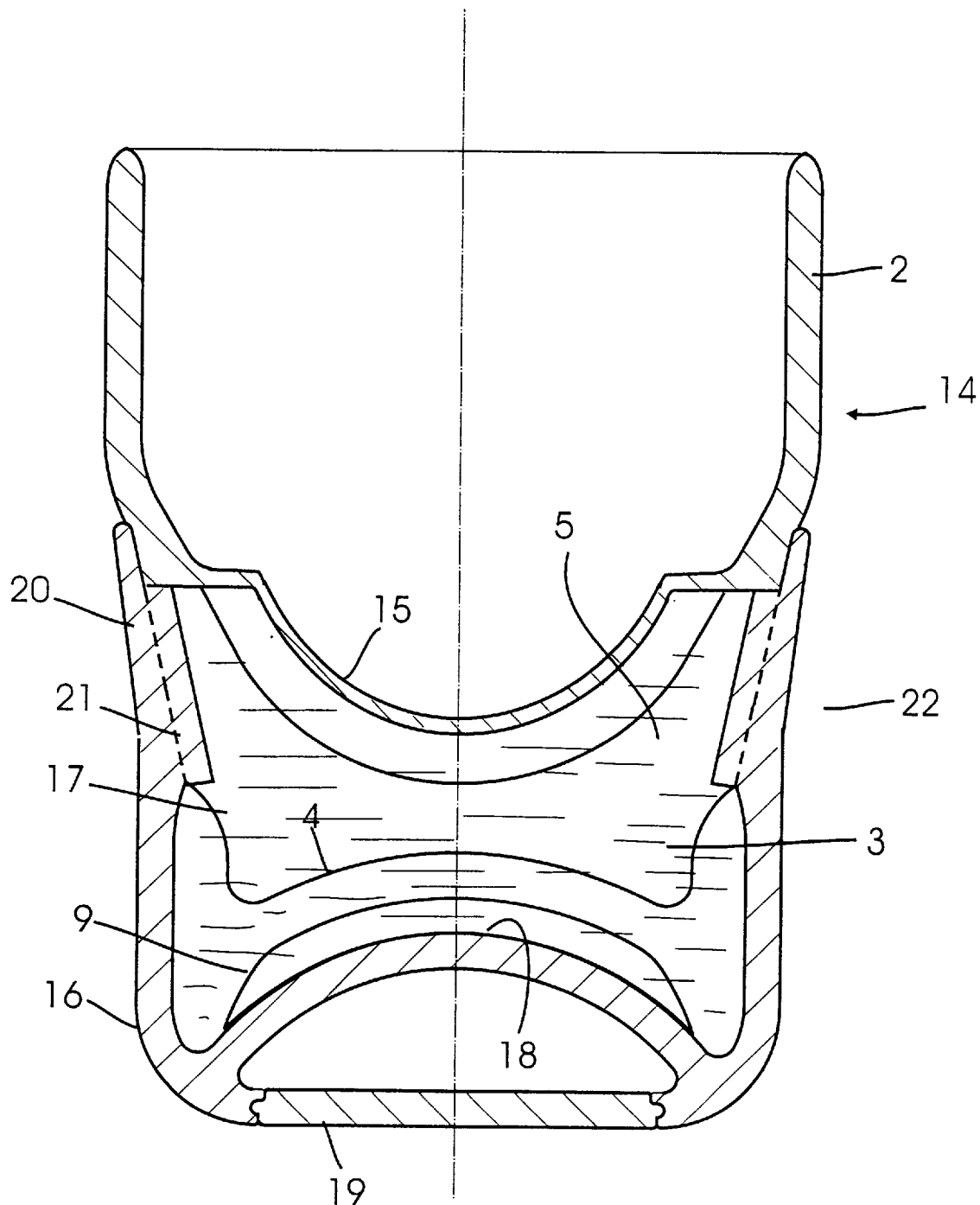
FIG. 10 shows the manipulator of FIGS. 7 to 9 as a part of a package or container for sterilely storing a contact lens.

When the contact lens is a reusable lens, it may be stored sterilely in the cup 16 shown in FIG. 10 until the contact lens is to be used again. The cup is filled with a disinfectant fluid 17, for example sterile saline solution of a suitable concentration.

The manipulator 14 with the contact lens 9 in FIGS. 4–6 being removed is then placed as a lid on the cup 16 after which the contact lens sinks down onto the convex support surface 18 of the cup, with the surface having a concave shape complementary to the convex face of the contact lens. The contact lens is therefore supported in a dimensionally stable manner during storage.

In FIG. 10, a second embodiment 14 of the manipulator according to the invention shown in FIGS. 7 to 9 is seen in an axial sectional view lengthwise of the slit 5. The cup 16 has a base 19 and a casing 20 which on the inside has two opposite ribs 21 fitting tightly into the slit 5 in each side of the skirt 2 of the manipulator. When the manipulator 14 is placed on the cup 16 shown in FIG. 10, the two parts 14 and 16 thus together form a sealed container 22 for sterile storage of the contact lens.

When the contact lens is to be used again, the container 22 is turned after which the contact lens will settle on the concave face 4 of the manipulator 14. After that, the cup 16 is removed and the manipulator used in conventional manner to apply the contact lens in the user's eye.

The manipulator 14 and the cup 16 can in some cases be individual parts that only are joined to a sealed container when a reusable lens is to be stored temporarily.

However according to the invention, the container 22 preliminarily constitutes a package for a new contact lens that can be either a disposable lens or a reusable lens.

When the contact lens is a reusable lens, the package is then advantageously used in the manner described above as container for temporarily storing a reusable lens until it is to be used again.

As can be seen, the manipulator according to the invention is thus universally applicable for both applying a contact lens in an eye and later for removing the applied contact lens from the eye.

Together with the cup 16, the manipulator 14 furthermore forms a simple package 22 for a new contact lens and after having been taken into use, the package is advantageously utilized several times as container 22 for temporary, sterile storage of the contact lens in a disinfectant fluid, for example sterile saline solution of an suitable concentration.

Figure 11:
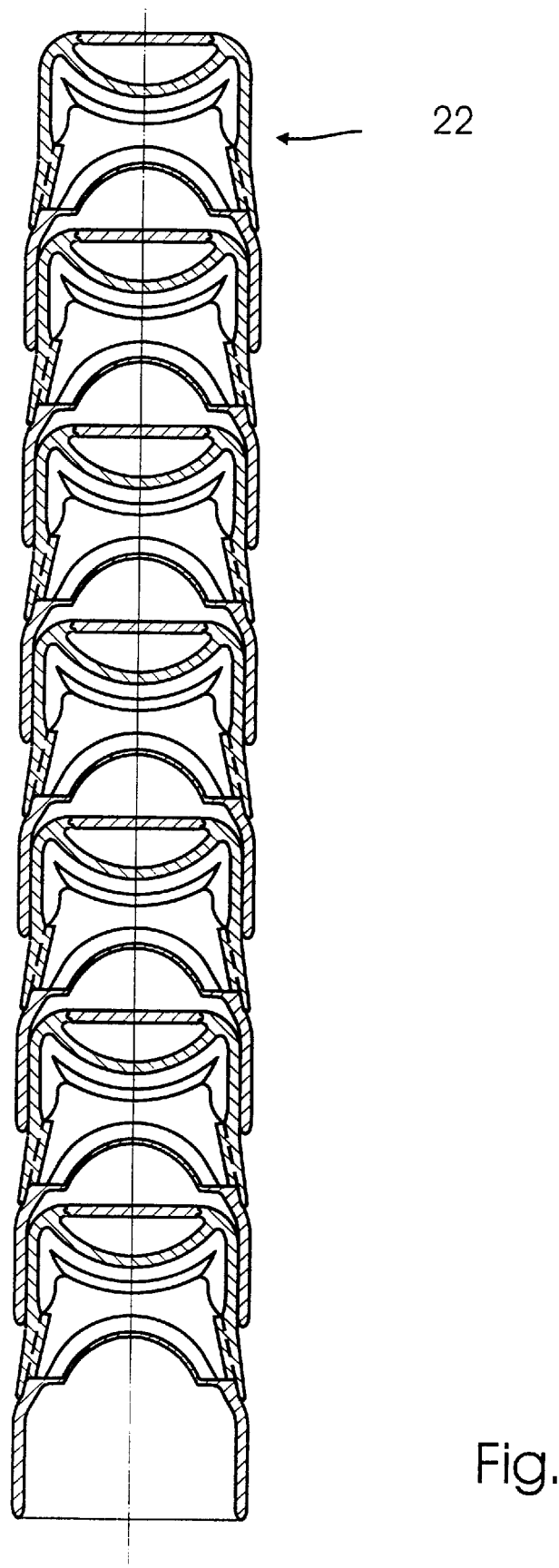
FIG. 11 shows a number of the packages or containers in FIG. 10 joined in a row.

The package 22 can be a single package but a number of these packages can also be delivered joined together in a row as shown in FIG. 11.

Figure 13:
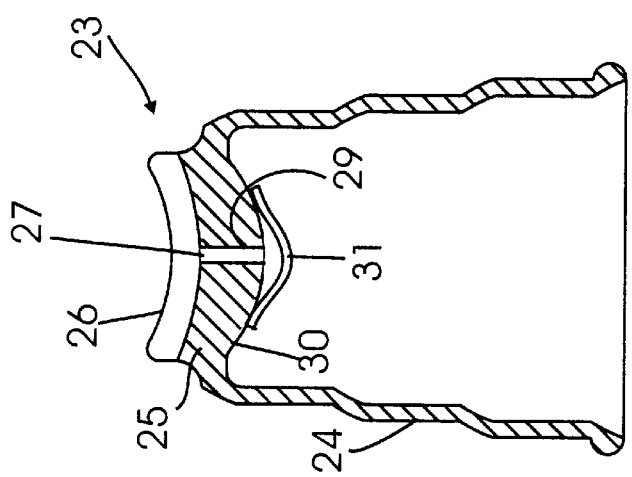
FIG. 13 shows the manipulator in FIG. 12 but rotated 90° in relation to FIG. 12.
Figure 12:
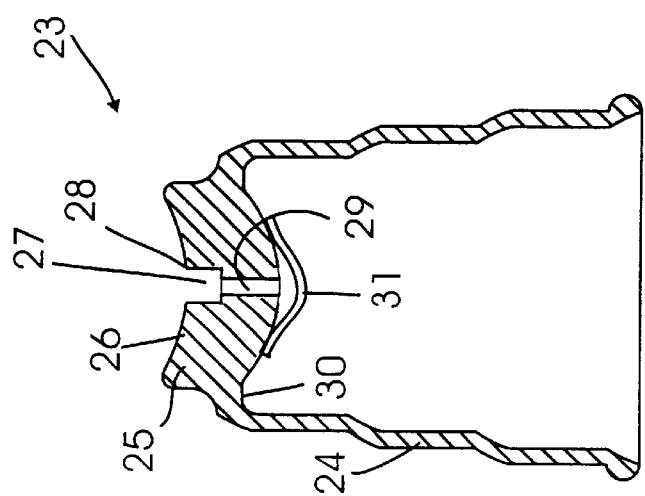
FIG. 12 is an axial sectional view of a third embodiment of a manipulator according to the invention.

FIGS. 12 and 13 show a third embodiment 23 of a manipulator according to the invention. This manipulator has a stepped skirt 24 and a base 25 with a concave face 26. Across the base is made a slit 27 with edges 28 that have a small curvature.

In this case, the slit 27 only extends a distance down into the base while a centrally placed channel 29 instead serves for connecting the slit to the underside 30 of the base. Under the mouth of the channel 29 on the underside 30 of the base is placed an elastic membrane 31 of e.g. rubber. Along the periphery, the membrane is joined with the base whereas it in a center area is distanced from the base. When the membrane is pressed in towards the base of the manipulator and is let go again so that it elastically returns to its original shape, with the membrane acting as a vacuum pump.

This function is used for drawing a fold into the slit 27 of the manipulator when the user is to remove a contact lens from his eye. The course of this operation moreover takes place in the same way as shown in FIGS. 4 to 6 and as described above except that the fold is drawn in instead of being pressed into the slit.

The elastic membrane 31 is according to the invention designed with such a short stroke that the produced negative pressure is only able to draw the fold exactly so far into the slit of the manipulator as is desired.

The third embodiment 23 of the manipulator according to the invention is also well suited for applying a contact lens in an eye. In this case, the elastic membrane 31 is used first for adhering a contact lens onto the concave face 26 of the manipulator base. When the contact lens is in contact with the eye, the user neutralizes the negative pressure with a light touch after which the manipulator can be removed just like that from the contact lens which now easily and safely has been applied in the eye.

The manipulator 23 can thus be used many times for applying a contact lens in an eye and subsequently for removing the lens. It is therefore important that the manipulator is stored sterilely when it is not in use.

Such a sterile storage can take place in the principle shown in FIG. 10 in which the manipulator is placed on a cup (not shown) with a disinfectant fluid, e.g. saline solution, the membrane during this being pressed home. When the membrane then is let go, the fluid from the cup is drawn into the slit 27, the channel 29 and the space between the underside 30 of the manipulator base and the membrane 31.

Figure 14:
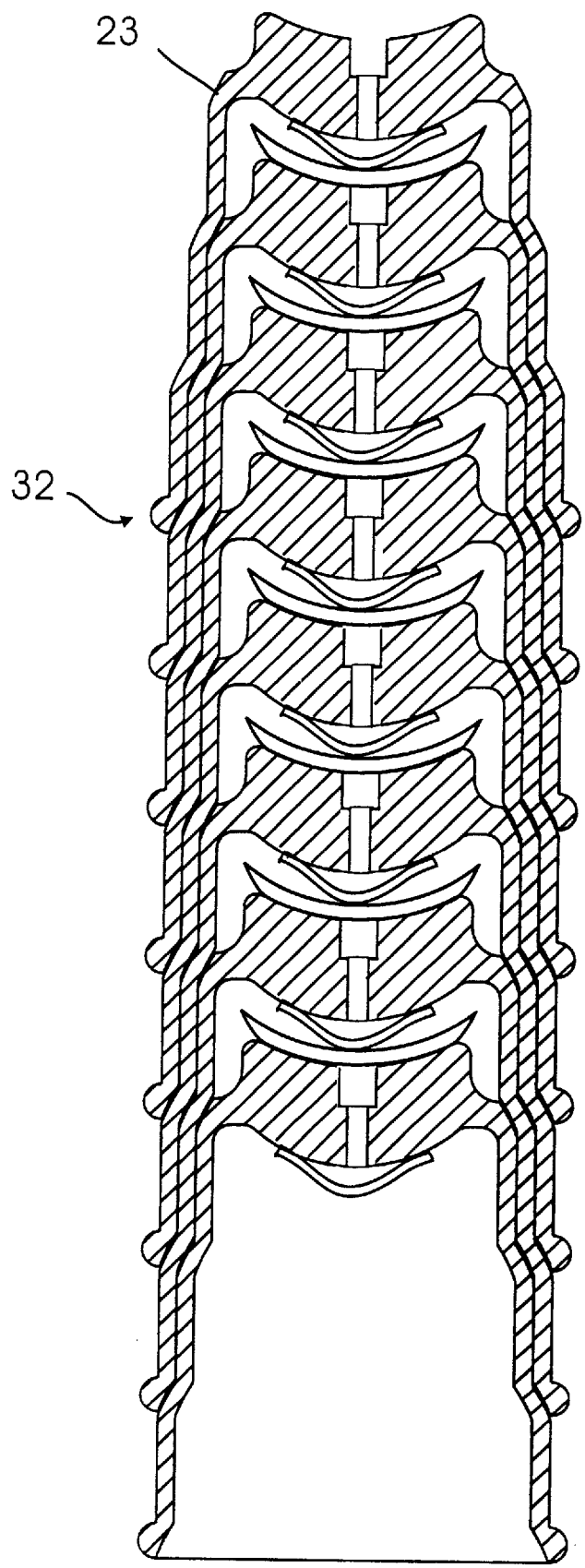
FIG. 14 shows a number of the manipulators in FIGS. 12 and 13 joined in a row.

FIG. 14 shows how a number of the manipulators of FIGS. 11 and 12 are joined together in a row 32. Between each of two adjacent manipulators, a chamber is defined with a contact lens placed in saline solution of suitable concentration. The topmost manipulator in the row which does not contain a contact lens acts as a lid over the subjacent chamber.

In FIG. 14 all the manipulators are of the kind shown in FIGS. 12 and 13.

Alternatively, only the topmost manipulator can be of this kind whereas the rest of the manipulators in the row are without slit and therefore only suited for applying a contact lens in an eye. The topmost manipulator provided with a slit is then used to remove the contact lenses that are applied in the user's eyes. In this case, the used contact lenses will typically be disposable lenses.

When the topmost manipulator is not is use, it is placed on a cup with a disinfectant fluid, e.g., a sterile saline solution of suitable solution in the same way as described above.

Figure 15:
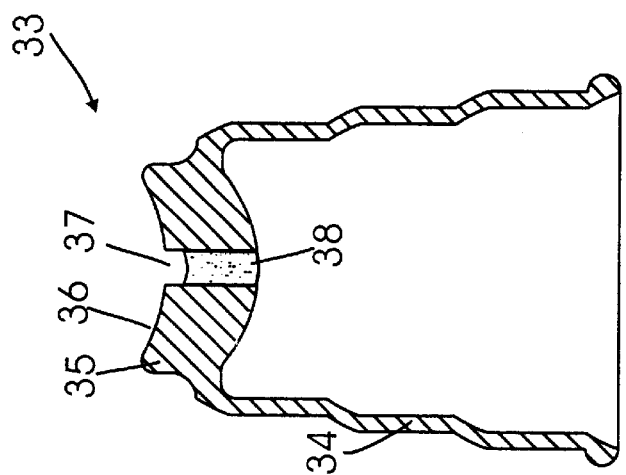
FIG. 15 is an axial sectional view of a fourth embodiment 33 of a manipulator according to the invention.

FIG. 15 shows a fourth embodiment 33 of a manipulator according to the invention. The manipulator 33 has a stepped skirt 34 and a base 35 with a concave face 36. Across the base 35 is made a slit 37 with a liquid-absorbent material 38, for example liquid-absorbent paper or cellular plastic.

The liquid-absorbent material can in one embodiment extend up to the concave face 36 of the base so that the contact lens upon removal of a contact lens from an eye adheres directly to the material when the concave face 36 of the manipulator is put in contact with the contact lens.

In a preferred second embodiment, the top face of the liquid-absorbent material is however placed at a distance from the concave face 36 of the manipulator which upon contact with the contact lens is moistened by the human saline solution on the contact lens. Some of this saline solution will enter into the slit 37 and be absorbed by the liquid-absorbent material 38 whereby the saline solution draws a fold with it into the slit. The manipulator 33 then functions in the way described above in the other embodiments.

The invention is described above on the assumption that the manipulator was designed as a fingerstall and that in the base of this fingerstall was made a slit extending across the base. Within the scope of the invention, the manipulator can however also be shaped as a bar forming the manipulation part and ending in a supporting part with a slit.

Different ways are shown in the drawing and described above of how conventional applicators and manipulators according to the invention can be combined. These combinations are only to be taken as examples as conventional applicators and manipulators according to the invention can be combined in many other expedient ways within the scope of the invention.

Instead of only one slit, there can be several slits that not necessarily are extending across the base but instead can be extending radially outwards from a central area on the base.

The sight can furthermore be designed in a way other than shown in the drawing, i.e. as a central line crossing the slit in cross direction.

Thus, the sight can instead consist of a number of concentric circles having the same center as the base or be a combination of this and above straight line embodiments.

What is claimed is:

1. A manipulator for applying a contact lens in or removing it from a user's eye and of the kind comprising,
    a manipulation part for manipulating the manipulator by a user's fingers,
    a supporting part on the manipulation part for supporting a contact lens having a convex face,
    a concave face on the supporting part for receiving and detachably retaining the convex face of the contact lens, and
    at least one slit in the concave face of the supporting part, wherein:
    the manipulator is designed as a fingerstall,
    the fingerstall comprises a skirt forming the manipulation part of the manipulator and a base forming its supporting part,
    the skirt comprises a substantially cylindrical end section and a substantially conically shaped base section,
    the base section comprises the concave face and at least a part of the at least one slit; and
    the outer wall of the conically shaped base section constitutes a gripping surface for the user's fingers.

2. The manipulator of claim 1, wherein the at least one slit passes into the concave face of its supporting part along edges with a slight curvature.

3. The manipulator of claim 1, wherein a number of said manipulators are joined together in a row wherein two adjacent manipulators define a chamber serving for storing a contact lens.

4. The manipulator of claim 1, which is also used for storing a contact lens in a contact lens storage solution.

5. A device for storing a contact lens which comprises at least two manipulators of claim 1 associated together in a row to define a chamber that can contain a sterile solution for receiving and storing the contact lens therein.

6. A method for inserting or removing a contact lens into or from a person's eye which comprises providing the manipulator of claim 1, and engaging the lens with the slit for inserting the lens into a person's eye or for removing the lens from a person's eye.

7. The method of claim 6 which further comprises including in the manipulator a sterile solution for storing a contact lens, placing a contact lens into the solution, and providing a cap for the manipulator so that the lens and solution can be retained safely therein.

8. The manipulator of claim 1 which is made of a transparent, elastic, plastic material.

9. The manipulator of claim 1 wherein the at least one slit has edges with a small curvature so that a contact lens can be received therein without damage.

10. A manipulator for applying a contact lens in or removing it from a user's eye and of the kind comprising, a manipulation part for manipulating the manipulator by a user's fingers, a supporting part on the manipulation part for supporting a contact lens having a convex face, a concave face on the supporting part for receiving and detachably retaining the convex face of the contact lens, and at least one slit in the concave face of the supporting part, wherein:

the manipulator is designed as a fingerstall, the fingerstall comprises a skirt forming the manipulation part of the manipulator and a base forming its supporting part, the skirt comprises a substantially cylindrical end section and a substantially conically shaped base section, the base section comprises the concave face and at least a part of the at least one slit; and the at least one slit extends completely or partly through the base of the fingerstall and a distance down along at least one side of its skirt.

11. A manipulator for applying a contact lens in or removing it from a user's eye and of the kind comprising, a manipulation part for manipulating the manipulator by a user's fingers, a supporting part on the manipulation part for supporting a contact lens having a convex face, a concave face on the supporting part for receiving and detachably retaining the convex face of the contact lens, and at least one slit in the concave face of the supporting part, wherein:

the manipulator is designed as a fingerstall, the fingerstall comprises a skirt forming the manipulation part of the manipulator and a base forming its supporting part, the skirt comprises a substantially cylindrical end section and a substantially conically shaped base section, the base section comprises the concave face and at least a part of the at least one slit; and the at least one slit has a mouth which defines its periphery and which further comprises an elastically deformable wall extending along and surrounding the mouth of the at least one slit on the inside of the fingerstall.

12. The manipulator of claim 11, wherein the elastically deformable wall is shaped as a U or a V.

13. The manipulator of claim 11, wherein the elastically deformable wall is shaped as a membrane.

14. A manipulator for applying a contact lens in or removing it from a user's eye and of the kind comprising, a manipulation part for manipulating the manipulator by a user's fingers, a supporting part on the manipulation part for supporting a contact lens having a convex face, a concave face on the supporting part for receiving and detachably retaining the convex face of the contact lens, and at least one slit in the concave face of the supporting part, wherein:

the manipulator is designed as a fingerstall, the fingerstall comprises a skirt forming the manipulation part of the manipulator and a base forming its supporting part, the skirt comprises a substantially cylindrical end section and a substantially conically shaped base section, the base section comprises the concave face and at least a part of the at least one slit; and the at least one slit is fitted with a liquid-absorbent material.

15. A device for storing a contact lens which comprises at least two manipulators, each comprising, a manipulation part for manipulating the manipulator by a user's fingers, a supporting part on the manipulation part for supporting a contact lens having a convex face, a concave face on the supporting part for receiving and detachably retaining the convex face of the contact lens, and at least one slit in the concave face of the supporting part, wherein:

the manipulator is designed as a fingerstall, the fingerstall comprises a skirt forming the manipulation part of the manipulator and a base forming its supporting part, the skirt comprises a substantially cylindrical end section and a substantially conically shaped base section, the base section comprises the concave face and at least a part of the at least one slit; and wherein the manipulators are nested together to form a chamber that can contain a sterile solution for receiving and storing the contact lens therein.

* * * * *